(12) United States Patent
Arnin

(10) Patent No.: US 11,364,060 B2
(45) Date of Patent: Jun. 21, 2022

(54) SPINAL SCREW WITH MOVABLE TIP

(71) Applicant: Apifix Ltd., Carmiel (IL)

(72) Inventor: Uri Arnin, Kiryat Tivon (IL)

(73) Assignee: ApiFix Ltd

( * ) Notice: Subject to any disclaimer, the term of this patent is extended or adjusted under 35 U.S.C. 154(b) by 112 days.

(21) Appl. No.: 16/475,687

(22) PCT Filed: Jan. 11, 2017

(86) PCT No.: PCT/IB2017/050133
§ 371 (c)(1),
(2) Date: Jul. 3, 2019

(87) PCT Pub. No.: WO2018/130877
PCT Pub. Date: Jul. 19, 2018

(65) Prior Publication Data
US 2019/0374271 A1    Dec. 12, 2019

(51) Int. Cl.
*A61B 17/86*    (2006.01)

(52) U.S. Cl.
CPC ........ *A61B 17/8685* (2013.01); *A61B 17/864* (2013.01); *A61B 17/863* (2013.01)

(58) Field of Classification Search
CPC .. A61B 17/8685; A61B 17/863; A61B 17/864
USPC .................................. 606/250–279, 300–330
See application file for complete search history.

(56) References Cited

U.S. PATENT DOCUMENTS

| | | | |
|---|---|---|---|
| 4,940,467 A * | 7/1990 | Tronzo | A61B 17/8875 606/66 |
| 2007/0260248 A1* | 11/2007 | Tipirneni | A61B 17/746 606/65 |
| 2009/0306718 A1* | 12/2009 | Tipirneni | A61B 17/685 606/263 |
| 2010/0312245 A1 | 12/2010 | Tipirneni | |
| 2010/0312292 A1 | 12/2010 | Tipirneni et al. | |
| 2011/0093020 A1* | 4/2011 | Wu | A61L 31/16 606/304 |
| 2016/0331553 A1 | 11/2016 | Tanaka et al. | |
| 2016/0374740 A1 | 12/2016 | Donald | |

FOREIGN PATENT DOCUMENTS

| | | |
|---|---|---|
| CN | 103813761 A | 5/2014 |
| CN | 204446072 U | 7/2015 |
| EP | 2676622 | 12/2013 |
| WO | 2015/172842 | 11/2015 |

OTHER PUBLICATIONS

PCT Search Report PCT/IB2017/050133, dated Jul. 26, 2017.
(Continued)

*Primary Examiner* — Eduardo C Robert
*Assistant Examiner* — Tara Rose E Carter
(74) *Attorney, Agent, or Firm* — Gerald W. Roberts; John V. Daniluck; Dentons Bingham Greenebaum LLP

(57) ABSTRACT

A spinal screw includes a shaft formed with a lumen and including a head, and a distal movable member including a distal tip and arranged to move in a distal portion of the lumen. A distal movable member (18) includes a proximal surface (24) arranged to abut against a stopper (26) formed in the shaft (12).

20 Claims, 3 Drawing Sheets

(56) References Cited

OTHER PUBLICATIONS

PCT IB2017/050133, Written Opinion, 5 pgs dated Jul. 19, 2017.
EP 17706301.3, EPO, Office Action, 6 pgs dated Jul. 1, 2020.
EP 17706301.3, Response Filed, 7 pgs dated Jan. 5, 2021.
JP 2019-536211, JPO, Office Action, 4 pgs dated Oct. 12, 2020.
Karame et al., "Biomechanical Evaluation of the Pedicle Screw Insertion Depth Effect on Screw Stability Under Cyclic Loading and Subsequent Pullout," J Spinal Disord Tech, vol. 28, No. 3, Apr. 2015.
JP 2019-53211, Response filed (English claims), 14 pgs dated Jun. 10, 2021.
JP 2019-53211, JPO, Decision of Refusal, 2 pgs (English translation), dated Jun. 30, 2021.
CN 20178008296.4, CNIPA, First Office Action, 7 pgs dated Oct. 22, 2021.

\* cited by examiner

SPINAL SCREW WITH MOVABLE TIP

FIELD OF THE INVENTION

The present invention relates generally to spinal implants and prostheses, and particularly to a spinal (e.g., pedicle) screw with a movable or sliding tip that can achieve a safe bi-cortical bone purchase when placed into a spinal vertebra.

BACKGROUND OF THE INVENTION

Spine degeneration of different types affects a significant portion of the population. Current surgical treatment involves multiple pedicle screws placed into the vertebrae.

Loosening of pedicle screws, mainly when the bone quality is sub-optimal, is a major problem. It is accepted however that bi-cortical bone purchase gives a much better stability to the screw. Surgeons are often afraid of getting true bi-cortical fixation because it is dangerous if the screw tip penetrates the anterior wall of the vertebrae. It is therefore desirable to achieve bi-cortical bone purchase without the risk of penetrating the anterior wall.

SUMMARY OF THE INVENTION

The present invention seeks to provide an improved spinal screw that can be extended by using a movable or sliding tip that can be advanced forwards after placing the screw into a vertebra, as is described more in detail hereinbelow. The spinal screw of the invention (which may be a pedicle screw) can achieve bi-cortical bone purchase without the risk of penetrating the anterior wall.

There is provided in accordance with an embodiment of the invention a spinal screw including a shaft formed with a lumen and including a head, a distal movable member including a distal tip and arranged to move in a distal portion of the lumen, and the distal movable member includes a proximal surface arranged to abut against a stopper formed in the shaft.

In accordance with an embodiment of the invention a biasing device is configured to provide an urging force on the distal movable member, such as a distally-directed urging force or a proximally-directed urging force on the distal movable member.

In accordance with an embodiment of the invention the distal tip is blunt or flat so that it cannot (or is very difficult to) penetrate the anterior wall of the vertebra.

In accordance with an embodiment of the invention the distal tip includes an additional stopper, e.g., a distally facing wall proximal to a distal-most point of the distal tip.

In accordance with an embodiment of the invention the distal tip includes one or more anti-rotation elements.

BRIEF DESCRIPTION OF DRAWINGS

The present invention will be understood and appreciated more fully from the following detailed description, taken in conjunction with the drawings in which.

DETAILED DESCRIPTION OF EMBODIMENTS

Figure 1A:
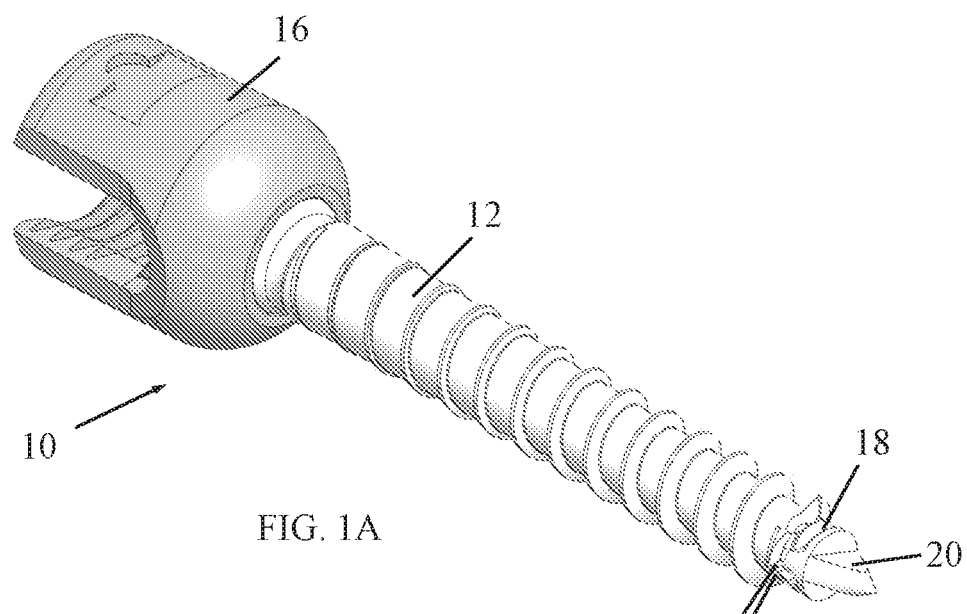
FIGS. 1A and 1B are simplified pictorial illustrations of a spinal screw in an initial contracted configuration and an extend configuration, respectively, constructed and operative in accordance with a non-limiting embodiment of the invention.
Figure 1B:
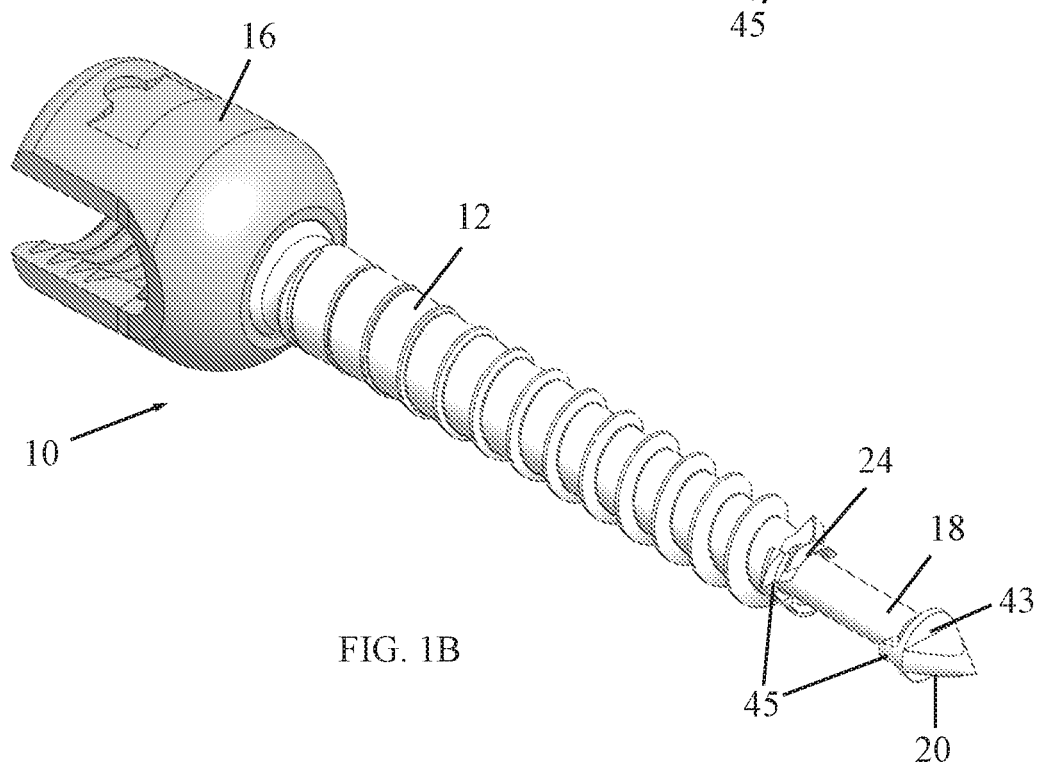
Figure 2:
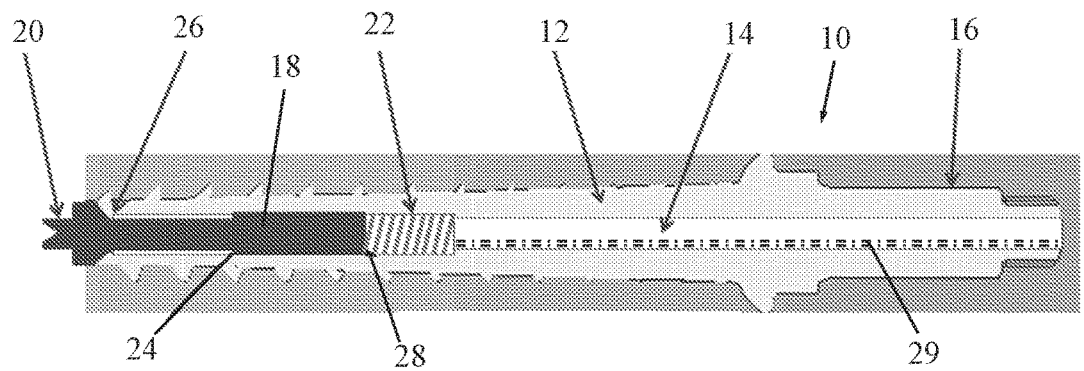
FIG. 2 is a simplified schematic illustration of the spinal screw in the initial contracted configuration.

Reference is now made to FIGS. 1A, 1B and 2, which illustrate a spinal screw 10, constructed and operative in accordance with a non-limiting embodiment of the invention.

The spinal screw 10 includes a shaft 12 which may be cannulated, that is, formed with a lumen 14 (FIG. 2). The spinal screw 10 includes a head 16, which may be polyaxial. The spinal screw 10 includes a distal movable member 18 arranged to move in the distal portion of lumen 14. The distal movable member 18 includes a distal tip 20. A biasing device 22 (FIG. 2), such as a coil spring, may be disposed in lumen 14 proximal to distal movable member 18, and urges distal movable member 18 to move in the distal direction (or alternatively in the proximal direction, as described below). Other types of biasing devices may be used, such as but not limited to, pneumatic, hydraulic or electric actuators. In other embodiments, there is no need for a biasing device; instead a tool may be used to move the distal movable member 18 either in the distal or proximal direction.

Figure 3:
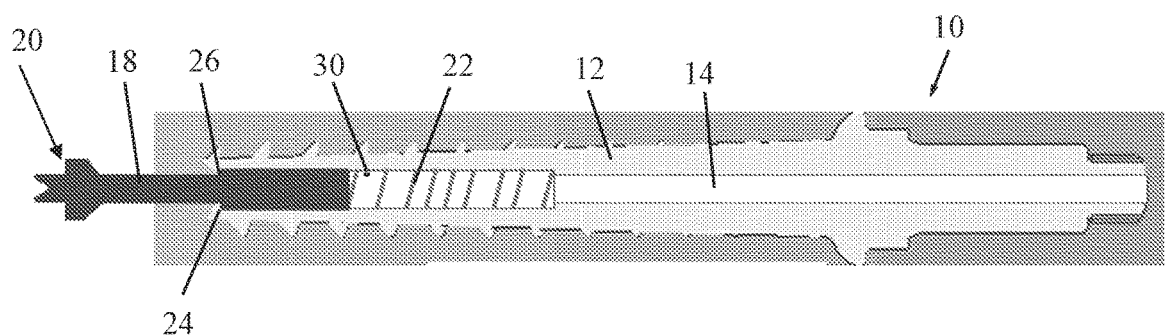
FIG. 3 is a simplified schematic illustration of the spinal screw in the extended configuration.

The distal movable member 18 includes a proximal surface 24 (FIGS. 1B and 2) arranged to abut against a stopper 26 (FIG. 2) formed in shaft 12. For example, stopper 26 may be a distal wall or shoulder formed in lumen 14 (e.g., lumen 14 may be counterbored to form the stopper). As seen in FIG. 3, when biasing device 22 has moved distal movable member 18 to the extended configuration, proximal surface 24 abuts against stopper 26, thereby stopping further distal movement of distal movable member 18. Stopper 26 does not interfere with proximal movement of distal movable member 18, so that distal movable member 18 can be retracted into shaft 12, if it is desired to remove the screw 10, such as for moving it to another installation site.

The distal tip 20 of distal movable member 18 may include an additional stopper 43 (FIG. 1B), such as a distally facing wall proximal to the distal-most point of distal tip 20. The additional stopper 43 abuts against spinal bone tissue to prevent the distal tip 20 from penetrating the anterior wall of the vertebra.

In one embodiment, biasing device 22 may be initially held in the compressed state (in tension) by a latch 28. Upon releasing the latch 28 (such as with a tool 29, shown in broken lines in FIG. 2, inserted in lumen 14), the biasing device 22 urges distal movable member 18 to the extended configuration.

In another embodiment, biasing device 22 is not initially in tension in its compressed state. Instead, the distal movable member 18 is connected to the biasing device 22 and the biasing device 22 is only used to retract distal movable member 18 back into shaft 12. The distal movable member 18 may be moved distally by a tool inserted in lumen 14 and pushed to the desired distal position. The distal movable member 18 may be held at the desired extended position by a catch 30 (FIG. 3). More than one catch 30 may be provided so that the surgeon has the choice of several extended positions for the distal movable member 18. The catch 30 may be released by a tool inserted in lumen 14, whereupon biasing device 22 retracts distal movable member 18 back into shaft 12.

In one embodiment, the distal tip 20 of distal movable member 18 may be round, so that when the screw 10 is rotated, the distal tip 20 does not change its rotational orientation.

In another embodiment, the distal tip 20 of distal movable member 18 may not be round, but instead square, rectangular, polygonal and the like, so that when the screw 10 is rotated, the distal tip 20 does change its rotational orientation.

In another embodiment, the cross section of the distal movable member 18 can vary along its length so that in the contracted position, when the screw 10 is rotated the distal tip 20 rotates with it, but as the distal movable member 18 is moved forwards (i.e., distally), the distal tip 20 no longer rotates with the screw 10. For example, in one embodiment, the distal tip 20 includes one or more anti-rotation elements 45 (FIGS. 1A and 1B), such as but not limited to, mating male and female keys 45. In the contracted orientation (FIG. 1A), the anti-rotation elements 45 are mated together so distal tip 20 rotates together with the rest of the screw. In the expanded orientation (FIG. 1B), the anti-rotation elements 45 are separated from each other so distal tip 20 does not rotate together with the rest of the screw.

In another embodiment, the distal tip 20 can be blunt or flat so that it cannot (or is very difficult to) penetrate the anterior wall of the vertebra.

The bone-interface surfaces of screw 10 may be configured to promote osseointegration, such as being roughened with knurling, acid-etching, grit blasting, and/or machining or other suitable methods. Additionally or alternatively, the bone-interface surfaces can be coated to promote osseointegration. Calcium phosphate ceramics, such as tricalcium phosphate (TCP) and hydroxyapatite (HA) are examples of materials that can enhance osseointegration of the bone-interface surfaces. Additionally or alternatively, the bone-interface surfaces can include macroscopic structures, such as, for example, threads, micro-threads, indentations, and/or grooves that are configured to promote osseointegration and can be used alone or combined with the roughening and/or the coatings described above.

Figure 4:
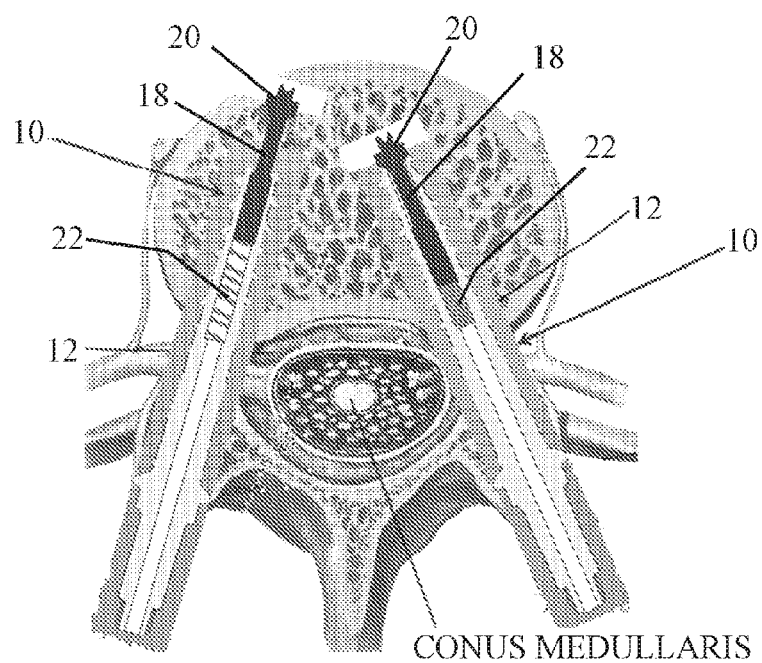
FIG. 4 is a simplified pictorial illustration of a spinal vertebra with the screw in its two configurations, that is, contracted and extended, in accordance with an embodiment of the invention.

Reference is now made to FIG. 4, which illustrates one spinal screw 10 in the contracted orientation (on the right) and in the extended orientation (on the left). It is seen that in the extended orientation, the screw 10 achieves bi-cortical bone purchase without the risk of penetrating the anterior wall of the vertebra.

What is claimed is:

1. A spinal screw, comprising:
   an externally threaded shaft formed with a lumen and comprising a head;
   a biasing device configured to provide an urging force and disposed in said lumen of said externally threaded shaft;
   a distal movable member comprising a distal tip and arranged to move in a distal portion of said lumen of said externally threaded shaft, under the urging force provided by said biasing device, to move said distal tip away from said externally threaded shaft; and
   a latch operable to releasably hold said biasing device in a first state,
   wherein said distal movable member comprises a surface arranged to abut against a stopper formed in said lumen of said externally threaded shaft, and
   wherein said biasing device is arranged to urge said distal movable member to move said distal tip away from said externally threaded shaft upon a release of said biasing device from said first state by said latch.

2. The spinal screw according to claim 1, wherein said stopper comprises a distal wall or shoulder formed in said lumen of said externally threaded shaft.

3. The spinal screw according to claim 1, wherein said first state is a compressed state.

4. The spinal screw according to claim 1, wherein said distal tip of said distal movable member is round.

5. The spinal screw according to claim 1, wherein a cross section of said distal movable member varies along its length.

6. The spinal screw according to claim 1, wherein said distal tip of said distal movable member is blunt or flat.

7. The spinal screw according to claim 1, wherein said distal tip comprises an additional stopper, wherein said additional stopper is configured to abut against bone tissue to prevent said distal tip from penetrating a vertebral wall, and wherein said additional stopper comprises a distally facing wall proximal to a distal-most point of said distal tip.

8. The spinal screw according to claim 7, wherein said distal tip comprises one or more anti-rotation elements.

9. The spinal screw according to claim 7, wherein said biasing device comprises at least one of a spring, a pneumatic actuator, a hydraulic actuator, and an electric actuator.

10. The spinal screw according to claim 9, wherein said biasing device consists of a spring.

11. A spinal screw, comprising:
    an externally threaded shaft formed with a lumen and comprising a head;
    a biasing device configured to provide an urging force and disposed in said lumen of said externally threaded shaft;
    a distal movable member comprising a distal tip and arranged to move in a distal portion of said lumen of said externally threaded shaft, under the urging force provided by said biasing device, to move said distal tip toward said externally threaded shaft; and
    a first catch operable to releasably hold said distal movable member in a first extended position,
    wherein said distal movable member comprises a surface arranged to abut against a stopper formed in said lumen of said externally threaded shaft, and
    wherein said biasing device is arranged to urge said distal movable member to move said distal tip toward said externally threaded shaft upon a release of said first catch.

12. The spinal screw according to claim 11, wherein said distal tip comprises an additional stopper, wherein said additional stopper is configured to abut against bone tissue to prevent said distal tip from penetrating a vertebral wall, and wherein said additional stopper comprises a distally facing wall proximal to a distal-most point of said distal tip.

13. The spinal screw according to claim 11, further comprising:
    a second catch operable to releasably hold said distal movable member in a second extended position,
    wherein said biasing device is arranged to urge said distal movable member to move said distal tip toward said externally threaded shaft upon a release of said second catch.

14. The spinal screw according to claim 13, wherein said distal tip of said distal movable member is round.

15. The spinal screw according to claim 13, wherein a cross section of said distal movable member varies along its length.

16. The spinal screw according to claim 13, wherein said distal tip of said distal movable member is blunt or flat.

17. The spinal screw according to claim 13, wherein said distal tip comprises an additional stopper, wherein said additional stopper is configured to abut against bone tissue to prevent said distal tip from penetrating a vertebral wall, and wherein said additional stopper comprises a distally facing wall proximal to a distal-most point of said distal tip.

18. The spinal screw according to claim 13, wherein said biasing device comprises at least one of a spring, a pneumatic actuator, a hydraulic actuator, and an electric actuator.

19. The spinal screw according to claim 13, wherein said biasing device consists of a spring.

20. The spinal screw according to claim 13, wherein said stopper comprises a distal wall or shoulder formed in said lumen of said externally threaded shaft.

\* \* \* \* \*